(12) United States Patent
Tang et al.

(10) Patent No.: US 11,896,431 B2
(45) Date of Patent: Feb. 13, 2024

(54) LINEAR SCANNING MECHANICAL VOLUME PROBE

(71) Applicant: Shenzhen Sonosray Technology Co., Ltd., Shenzhen (CN)

(72) Inventors: Shengli Tang, Shenzhen (CN); Xiaoyan Li, Shenzhen (CN)

(73) Assignee: Shenzhen Sonosray Technology Co., Ltd., Shenzhen (CN)

(*) Notice: Subject to any disclaimer, the term of this patent is extended or adjusted under 35 U.S.C. 154(b) by 0 days.

(21) Appl. No.: 18/181,413

(22) Filed: Mar. 9, 2023

(65) Prior Publication Data
US 2023/0414199 A1 Dec. 28, 2023

(30) Foreign Application Priority Data

Jun. 27, 2022 (CN) .......................... 202210734218.4

(51) Int. Cl.
*A61B 8/00* (2006.01)
*A61B 8/08* (2006.01)

(52) U.S. Cl.
CPC ............ *A61B 8/4461* (2013.01); *A61B 8/483* (2013.01)

(58) Field of Classification Search
None
See application file for complete search history.

(56) References Cited

U.S. PATENT DOCUMENTS

2011/0320143 A1* 12/2011 Hopkins ................ G10K 11/35
702/56

FOREIGN PATENT DOCUMENTS

| CN | 102018531 A | 4/2011 |
| CN | 103006262 A | 4/2013 |
| CN | 103690190 A | 4/2014 |
| CN | 104224228 A | 12/2014 |
| CN | 204181645 U | 3/2015 |
| CN | 111089900 A | 5/2020 |
| TW | M334123 U | 6/2008 |

OTHER PUBLICATIONS

First Office Action issued in counterpart Chinese Patent Application No. 202210734218.4, dated Oct. 28, 2022.

* cited by examiner

*Primary Examiner* — Shahdeep Mohammed
(74) *Attorney, Agent, or Firm* — Westbridge IP LLC (57) ABSTRACT

Disclosed is a linear scanning mechanical volume probe comprising a bracket on which a drive wheel, a first reverse wheel and a second reverse wheel are provided, an axis of the drive wheel, an axis of the first reverse wheel and an axis of the second reverse wheel are parallel; a guide rod is further provided on the bracket, and the axis of the guide rod is perpendicular to the axis of the drive wheel, a slider which can slide axially along the guide rod is provided on the guide rod, a transducer is fixedly connected to the slider; the first reverse wheel and the second reverse wheel are respectively provided near opposite ends of the guide rod, and further comprise a first rope and a second rope. The linear scanning mechanical volume probe can ensure that a high resolution image can be obtained at a distance from the transducer.

8 Claims, 6 Drawing Sheets

LINEAR SCANNING MECHANICAL VOLUME PROBE

CROSS-REFERENCE TO RELATED APPLICATIONS

The present application claims priority to Chinese Patent Application No. 202210734218.4, filed on Jun. 27, 2022, the content of which is incorporated herein by reference in its entirety.

TECHNICAL FIELD

The present application relates to the technical field of medical ultrasound imaging devices, in particular to a linear scanning mechanical volume probe.

BACKGROUND

The mechanical volume probe is an ultrasonic probe for three-dimensional imaging using an ultrasonic imaging system, which operates as follows: the ultrasonic imaging system controls rotation of a motor inside the probe, and the motor drives a transducer to swing back and forth in a certain range via a transmission system, and in the process of swinging, the transducer transmits ultrasonic waves at a certain distance and receives echoes with human tissue information, and then the two-dimensional information collected at different positions is processed by the ultrasonic imaging system and synthesized into a three-dimensional image.

At present, the transducer in the mechanical volume probe is generally scanned along an arc trajectory, and two-dimensional plane information is collected at a certain angle interval by the transducer. Since the acquisition planes are distributed divergently, at a distance from the transducer, the distance between points on adjacent acquisition planes is larger, resulting in a reduced image resolution, and it is difficult to obtain a clear image at a distance from the transducer.

SUMMARY

The technical problem to be solved by the present application is to provide a linear scanning mechanical volume probe with a acquisition plane distributed in parallel.

In order to solve the above technical problem, a technical solution adopted by the present application is as follows: a linear scanning mechanical volume probe comprising a bracket on which a drive wheel, a first reverse wheel and a second reverse wheel that are respectively rotatable are provided, an axis of the drive wheel, an axis of the first reverse wheel and an axis of the second reverse wheel are parallel; a guide rod is further provided on the bracket, and the axis of the guide rod is perpendicular to the axis of the drive wheel, a slider which can slide axially along the guide rod is provided on the guide rod, and a transducer is fixedly connected to the slider; the first reverse wheel and the second reverse wheel are respectively provided near opposite ends of the guide rod, and further comprise a first rope and a second rope; two ends of the first rope are respectively connected to the drive wheel and the slider and the first rope is wound on the first reverse wheel, and two ends of the second rope are respectively connected to the drive wheel and the slider and the second rope is wound on the second reverse wheel.

An advantageous effect of the present application is that for the linear scanning mechanical volume probe provided by the present application, two ropes are used to respectively connect the drive wheel and the slider, and the two ropes are respectively wound on the surfaces of the two reverse wheels; when the drive wheel rotates, the ropes can pull the slider to move along the axial direction of the guide rod, thereby driving the transducer fixed on the slider to move along a linear trajectory and perform scanning; since the transducer scans linearly along the axis of the guide rod, the transducer acquisition planes are parallel to each other, and the distances of points on adjacent acquisition planes are the same regardless of the distance from the transducer, and the distances between points on the acquisition planes do not increase because of the distance from the transducer, ensuring that a high resolution image is also obtained at a distance from the transducer.

DETAILED DESCRIPTIONS OF THE EMBODIMENTS

In order to explain the technical contents, the objects, and the effects of the present application in detail, the embodiments will be described below with reference to the accompanying drawings.

Embodiment 1

Figure 1:
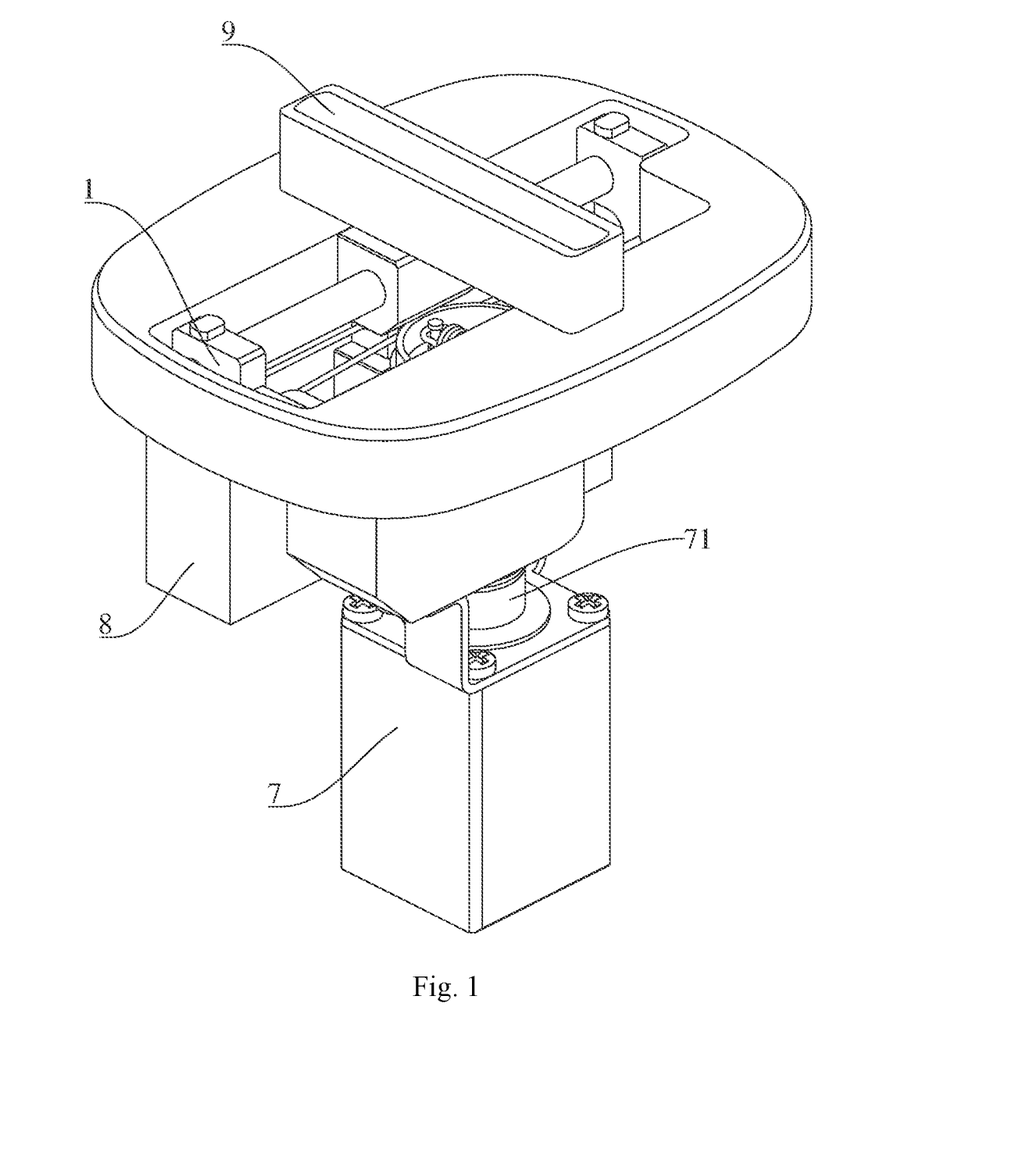
FIG. 1 is a schematic view showing a structure of a linear scanning mechanical volume probe according to Embodiment 1 of the present application.
Figure 2:
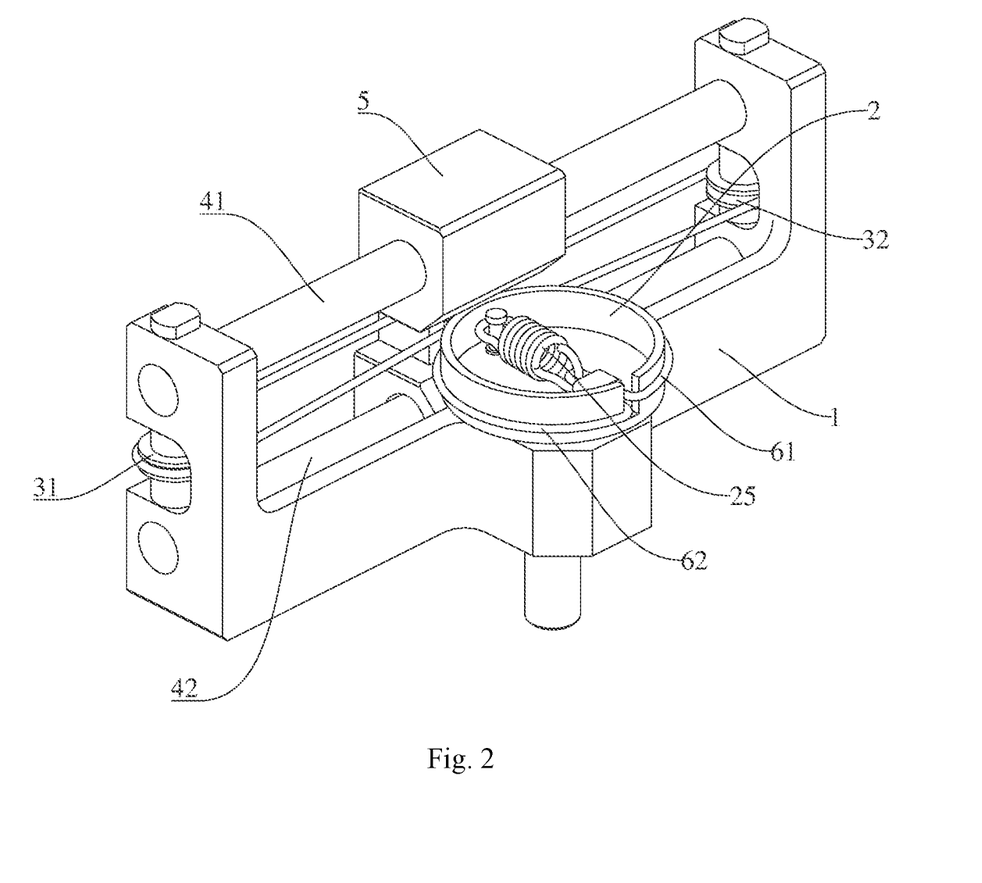
FIG. 2 is a partial structural diagram of a linear scanning mechanical volume probe according to Embodiment 1 of the present application.

As shown in FIGS. 1 and 2, Embodiment 1 of the present application is as follows: a linear scanning mechanical volume probe comprising a base 8 and a bracket 1 fixed on the base 8, wherein the bracket 1 is provided with a drive wheel 2, a first reverse wheel 31 and a second reverse wheel 32 which are respectively rotatable, an axis of the drive wheel 2, an axis of the first reverse wheel 31 and an axis of the second reverse wheel 32 are all in a vertical direction; a guide rod 41 and a guide rod 42 are further provided on the bracket 1, and the guide rod 41 is provided with a slider 5 which can slide in an axial direction of the guide rod 41, and the bottom of the slider 5 is slidable in the axial direction of the guide rod 42; the axial direction of the guide rod 41 is perpendicular to the axis of the drive wheel 2, that is to say, the axial direction of the guide rod 41 is a horizontal direction, the first reverse wheel 31 and the second reverse wheel 32 are respectively provided near two opposite ends of the guide rod 41, the slider 5 is fixedly connected to a transducer 9, and also comprises a first rope 61 and a second rope 62, two ends of the first rope 61 are respectively connected to the drive wheel 2 and the slider 5, and the first rope 61 is wound on the first reverse wheel 31; two ends of the second rope 62 are respectively connected to the drive wheel 2 and the slider 5, and the second rope 62 is wound on the second reverse wheel 32, and when the drive wheel 2 rotates clockwise, the second rope 62 pulls the slider 5 to move to the right; when the drive wheel 2 rotates counterclockwise, the first rope 61 pulls the slider 5 to move to the left. Therefore, when the drive wheel 2 reciprocates, the transducer 9 fixed to the slider 5 can be driven to reciprocate along a linear trajectory and scan.

Figure 3:
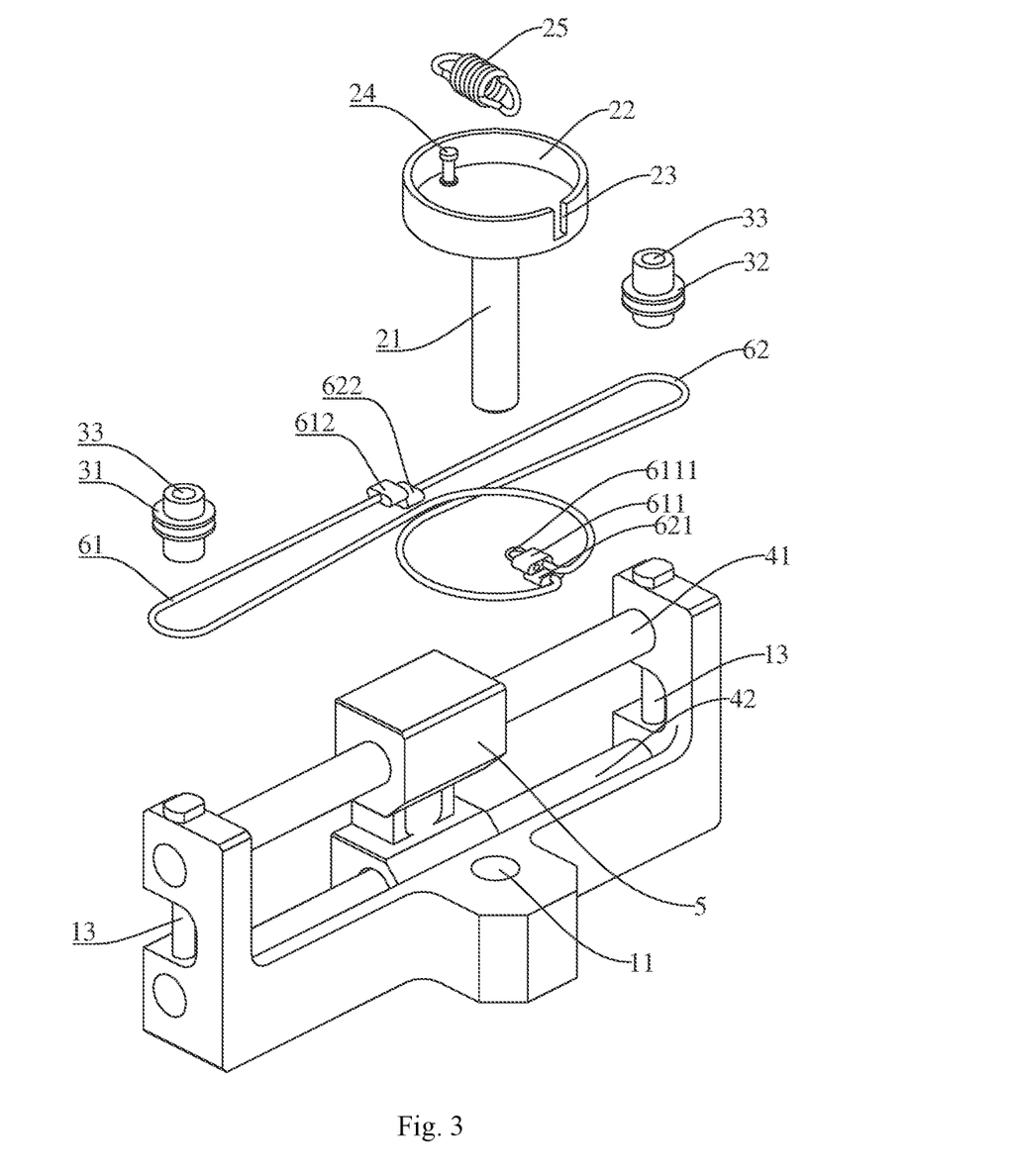
FIG. 3 is a partial exploded view of a partial structure in the linear scanning mechanical volume probe according to Embodiment 1 of the present application.

Specifically, as shown in FIGS. 1-3, a drive member 7 for driving the rotation of the drive wheel 2 is fixed on the base 8, the drive member 7 is an electric motor, the axis of the output shaft of the drive member 7 coincides with the axis of the drive wheel 2, and a coupling 71 is fixed at the end of the output shaft of the drive member 7. The drive wheel 2 has a rotating shaft 21 and the axis of the rotating shaft 21 is vertical; the bracket 1 is provided with a first hole 11 cooperating with the rotating shaft 21 and the rotating shaft 21 passes through one end of the first hole 11; and the rotating shaft 21 protrudes from the bracket 1. The bracket 1 is fixed to the base 8, and the rotating shaft 21 protrudes from the base 8 and is fixed to the coupling 71, so that the drive wheel 2 can rotate smoothly driven by the drive member 7. Since the drive member 7 is vertically provided on the base 8, the dimension of the drive member 7 in the direction perpendicular to the axis of the output shaft of the drive member 7 is generally small, and the drive member 7 can be received at the handle of the housing of the linear scanning mechanical volume probe, the layout of the internal components of the linear scanning mechanical volume probe can be optimized to reduce the required space, and then the overall dimension of the linear scanning mechanical volume probe can be optimized so that the linear scanning mechanical volume probe is easy to hold, and it is convenient for medical personnel to hold the linear scanning mechanical volume probe for movement for data acquisition operations.

Figure 4:
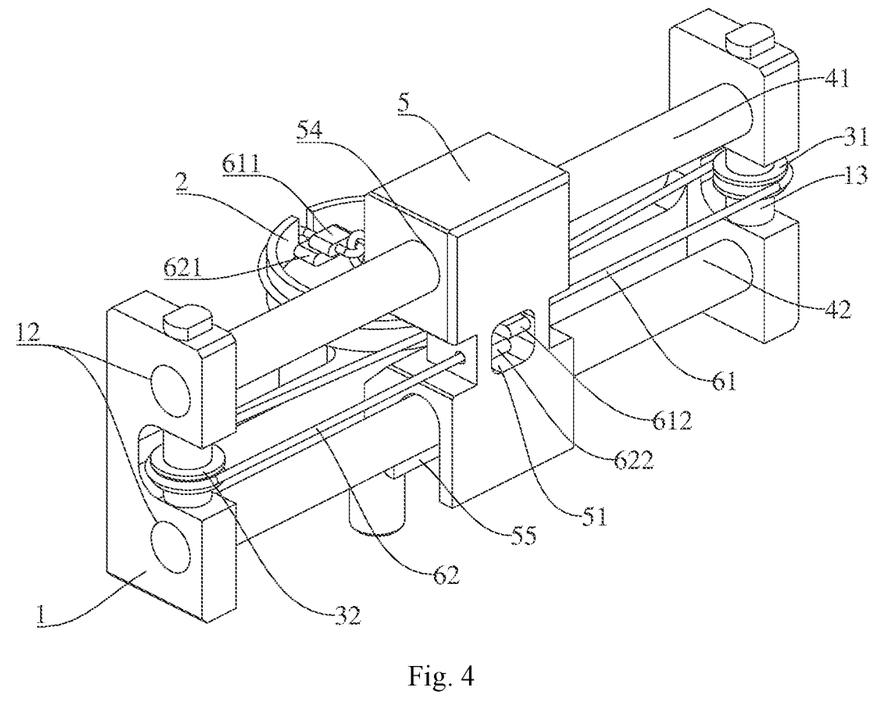
FIG. 4 is a schematic view showing another view of a part of the structure of the linear scanning mechanical volume probe according to Embodiment 1 of the present application.

As shown in FIGS. 3 and 4, in this embodiment, in order to realize the connection of the first rope 61 with the drive wheel 2 and the slider 5, one end of the opposite ends of the first rope 61 is provided with a first chuck 611, wherein the first chuck 611 forms a first clip 6111, and the other end of the first rope 61 is provided with a second chuck 612. A top surface of the drive wheel 2 has a concave receiving groove 22, and the side wall of the drive wheel 2 is provided with an opening 23 in communication with the receiving groove 22, and the receiving groove 22 is provided with a first pin 24. One end of the first spring 25 is hooked on the first pin 24 by a ring hook, the first chuck 611 passes through the opening 23 and extends into the receiving groove 22, and the first clip 6111 is hooked to the ring hook in one end of the first spring 25 to fix an end of the first rope 61 on the drive wheel 2. A slot 51 is provided on the slider 5, the other end of the first rope 61 passes through a hole (not shown) on the slider 5 and enters the slot 51, and a second chuck 612 is provided at the end of the first rope 61, the second chuck 612 is received in the slot 51 and abuts against the inner peripheral wall of the slot 51 to fix the other end of the first rope 61 on the slider 5, thereby connecting the first rope 61 with the drive wheel 2 and the slider 5. Accordingly, one end of the opposite ends of the second rope 62 is provided with a first chuck 621, and the other end is provided with a second chuck 622; the first chuck 621 passes through the opening 23 and extends into the receiving groove 22, and the first chuck 621 abuts against the inner peripheral wall of the receiving groove 22 to fix one end of the second rope 62 to the drive wheel 2. The other end of the second rope 62 passes through a hole (not shown) in the slider 5 and enters the slot 51, and a second chuck 622 is provided at the end of the second rope 62, and the second chuck 622 is received in the slot 51 and abuts against the inner peripheral wall of the slot 51 to fix the other end of the second rope 62 on the slider 5, thereby connecting the second rope 62 with the drive wheel 2 and the slider 5.

By means of the stretching and retraction deformation of the spring 25, both the first rope 61 and the second rope 62 can be kept in a tight state, so that when the drive wheel 2 rotates and pulls the first rope 61 and the second rope 62, the slider 5 can quickly respond to the action of the drive wheel 2 and move relative to the guide rod 4, preventing a delay in the action of the slider 5 from affecting the normal scanning of the transducer 9, especially when the drive wheel 2 rotates at a small angle, ensuring a corresponding displacement of the slider 5 to achieve a gapless transmission and a zero lag response. The spring 25 may be replaced by another form of spring or elastic member or the like having elasticity.

Referring to FIG. 3, the first rope 61 extends out of a notch 23 of the receiving groove 22 and is firstly wound on the drive wheel 2 in a clockwise direction for about half a circle, then extends to the left along a straight line, reaches the first reverse wheel 31, then is wound on the first reverse wheel 31 in a counterclockwise manner for about half a circle, then extends to the right along a straight line, and finally passes through the hole on the slider 5 and extends into the slot 51 on the slider 5. The second rope 62 extends out of the notch 23 of the receiving groove 22, is wound on the drive wheel 2 in a counterclockwise direction for about half a circle, then extends to the right along a straight line, reaches the second reverse wheel 32, is wound on the second reverse wheel 32 in a clockwise direction for about half a circle, then extends to the left along a straight line, and finally passes through the hole on the slider 5 and extends into the slot 51 of the slider 5.

With reference to FIGS. 3 and 4, a guide rod 41 and a guide rod 42 are a vertical direction on the bracket 1, and axes thereof are parallel to each other; the bracket 1 is provided with bracket 1 is provided with a second hole 12 (as shown in FIG. 4) for mounting the guide rod 41 and the guide rod 42, respectively; and the guide rods 41 and 42 extend into the second hole 12 and are fixed with the bracket 1 by means of bonding, screwing or clamping. The slider 5 is provided with a through hole 54 and a groove 55, the through hole 54 of the slider 5 is fitted with the pin hole of the guide rod 41, and the groove 55 is fitted with a side edge of the guide rod 42 to ensure that the slider 5 does not tilt when the slider 5 moves in the axial direction of the guide rod 41.

As shown in FIGS. 2 and 3, the first reverse wheel 31 is provided with a third hole 33, the axis of which coincides with the axis of the reverse wheel 31. A third pin 13 is fixed on the bracket 1, and the third pin 13 is rotatably engaged with the third hole 33 on the first reverse wheel 31 so that the first reverse wheel 31 can rotate around the third pin 13. A rotatable engagement of the second reverse wheel 32 with respect to the bracket 2 is achieved in the same way. The first rope 61 can pull the slider 5 to slide under the guidance of the first reverse wheel 31, and the second rope 62 can pull the slider 5 to slide under the guidance of the second reverse wheel 32.

With reference to FIGS. 1 and 2, the working process of the linear scanning mechanical volume probe provided by this embodiment is as follows: the transducer 9 is in an initial position, the drive member 7 is activated to drive the drive wheel 2 to rotate forward (clockwise or counterclockwise) around the vertical direction, with the action of the drive wheel 2, the first rope 61 or the second rope 62 drives the slider 5 to slide on the guide rod 41 under the pull of the drive wheel 2, at this moment, the transducer 9 fixed on the slider 5 moves along a linear trajectory and scans, and after the transducer 9 moves to a first pre-set position along the guide rod 41, the reverse rotation of the drive member 7 drives the drive wheel 2 to reverse around the vertical direction (opposite to the forward rotation direction), at this time, the second rope 62 or the first rope 61 pulls the slider 5 to slide on the guide rod 4 in the reverse direction, the drive member 7 again drives the drive wheel 2 to forward rotation after the transducer 9 moves to a second preset position along a linear trajectory, and the above-mentioned steps are repeated until the transducer 9 completes scanning along a preset path.

In this embodiment, for the convenience of assembly, the bracket 1 is provided separately from the base 8, and the bracket 1 is fixed to the base 8 after all the moving parts are installed. In practice, the bracket 1 and the base 8 may be one piece and the base 8 may be part of the bracket 1.

In this embodiment, one end of the rope passes through the opening 23 of the drive wheel and then bears the chuck on the inner wall of the receiving groove 22, and the other end passes through the hole of the slider and then bears the chuck on the inner wall of the receiving groove 51. It is also possible to fix the rope by pressing the rope with a screw, hooking the clip at the end of the rope on a pin, etc.

Embodiment 2

Figure 5:
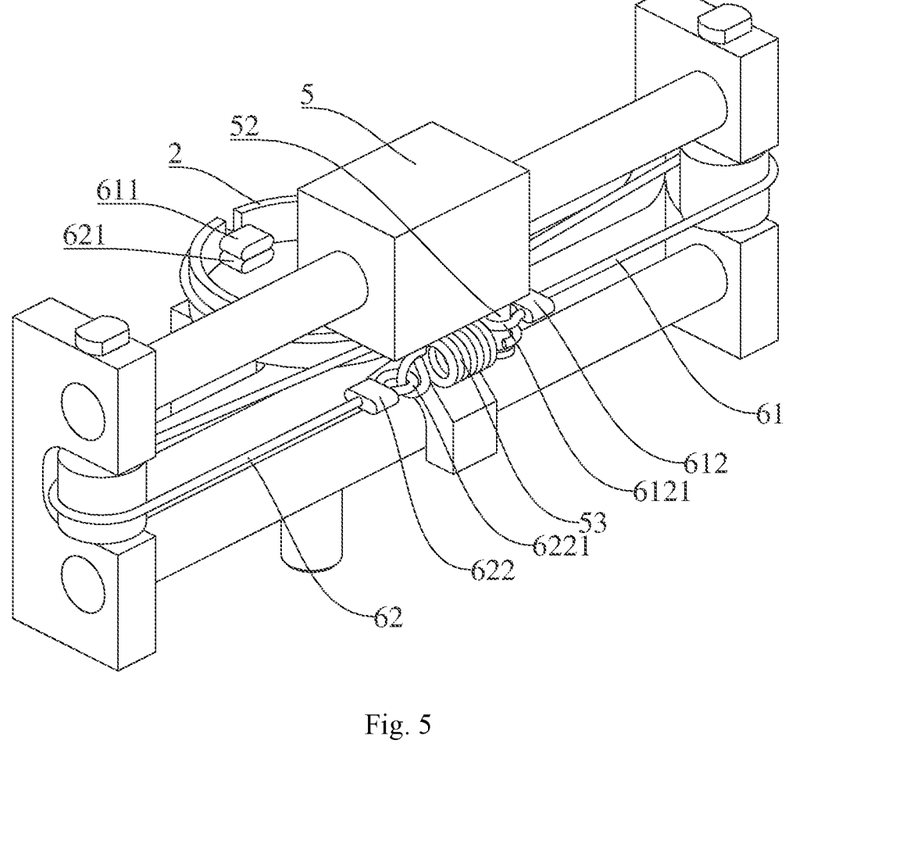
FIG. 5 is a partial structural diagram of a linear scanning mechanical volume probe according to Embodiment 2 of the present application.
Figure 6:
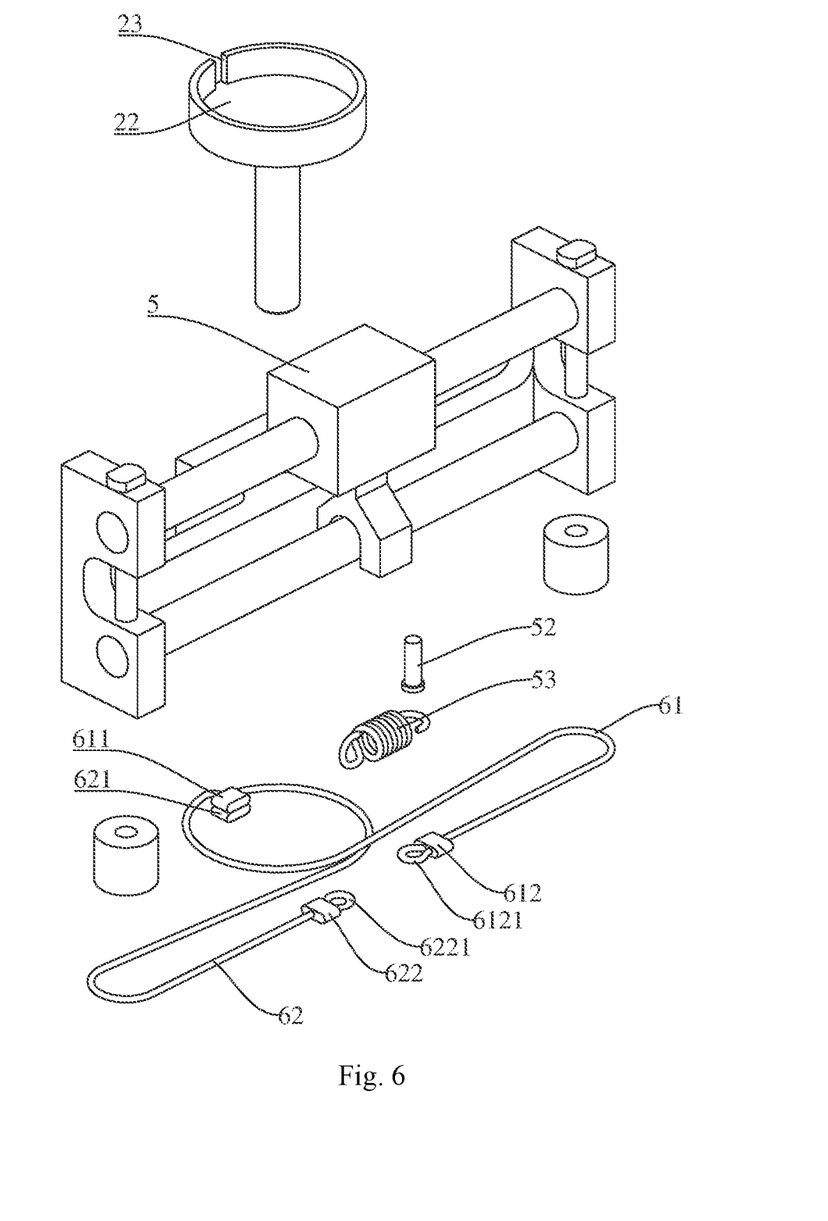
FIG. 6 is a partial exploded view of a partial structure in a linear scanning mechanical volume probe according to Embodiment 2 of the present application.

With reference to FIGS. 5 and 6, Embodiment 2 of the present application is another technical solution proposed on the basis of Embodiment 1 for the connection mode of the first rope 61 with the drive wheel 2 and the slider 5 and the connection mode of the second rope 62 with the drive wheel 2 and the slider 5, and differs from Embodiment 1 only in that the connection mode of the first rope 61 with the drive wheel 2 and the slider 5 and the connection mode of the second rope 62 with the drive wheel 2 and the slider 5 are different.

Please combine FIGS. 5 and 6. One of the opposite ends of the first rope 61 is provided with a first chuck 611, and the other end is provided with a second chuck 612, and the second chuck 612 forms a second clip 6121. The first chuck 611 passes through the opening 23 and extends into the receiving groove 22, and the first chuck 611 abuts against the inner peripheral wall of the receiving groove 22 to fix one end of the first rope 61 to the drive wheel 2. The slider is provided with a second pin 52, and the second clip 6121 is fitted over the second pin 52 to fix the other end of the first rope 61 to the slider 5. One of the opposite ends of the second rope 62 is provided with a first chuck 621, and the other end is provided with a second chuck 622, and the second chuck 622 forms a second clip 6221. The second rope 62 passes through the opening 23 and extends into the receiving groove 22, and the first chuck 621 abuts against the inner peripheral wall of the receiving groove 22 to fix one end of the second rope 62 to the drive wheel 2. One end of a second spring 53 is hooked to the second pin 52 by a ring hook and the other end is hooked to the second clip 6221 on the second rope 62.

By means of the stretching and retraction of the second spring 53, both the first rope 61 and the second rope 62 can be kept in a tight state, so that when the drive wheel 2 rotates and pulls the first rope 61 and the second rope 62, the slider 5 can quickly respond to the action of the drive wheel 2 and move relative to the guide rod 4, preventing a delay in the action of the slider 5 from affecting the normal scanning of the transducer 9, especially when the drive wheel 2 rotates at a small angle, ensuring a corresponding displacement of the slider 5 to achieve a gapless transmission and a zero lag response. The second spring 53 may be replaced by another form of spring or elastic member or the like having elasticity.

For Embodiment 1, the first spring 25 is received in the receiving groove 22 of the drive wheel 2, and the spring deformation range is limited by the size of the receiving groove 22. For Embodiment 2, the second spring 53 is located at the opening of the slider, making full use of the slider length dimension, resulting in a larger spring deflection range.

In summary, the linear scanning mechanical volume probe provided by the present application drives a drive wheel to rotate via a drive member to drive a rope to pull a slider to move along a guide to realize that the transducer moves along a linear trajectory, and can drive the slider to move back and forth on the guide rod by controlling the forward and reverse rotation of the drive member to enable the transducer to swing back and forth along a pre-set trajectory for scanning; and since the transducer scans linearly along the axis of the guide rod, the acquisition planes of the transducer are parallel to each other, regardless of the distance from the transducer, the distance between points on adjacent acquisition planes is the same, and the distance between points on the acquisition planes will not increase due to the distance from the transducer, so as to ensure that a high-definition image can be obtained at the distance from the transducer; the linear scanning mechanical volume probe uses a first elastic member provided on the drive wheel or a second elastic member provided on the slider to keep the rope in a tight state, to ensure that the rope can quickly respond to the action of the drive wheel and drive the slider to move, and prevent the action of the slider from delaying to affect the normal scanning of the transducer, especially when the drive wheel rotates at a small angle, ensuring that the slider produces a corresponding displacement, to achieve a gapless transmission and a zero-lag response.

The above description is only an embodiment of the present application, and is not intended to limit the scope of the present application, and all equivalent modifications made by the present application and the contents of the accompanying drawings, which are directly or indirectly applied to the related technical fields, are included in the scope of the present application.

What is claimed is:

1. A linear scanning mechanical volume probe, comprising:
   a bracket;
   a drive wheel rotatably mounted on the bracket;
   a first reverse wheel rotatably mounted on the bracket, an axis of the first reverse wheel being parallel to an axis of the drive wheel;
   a second reverse wheel rotatably mounted on the bracket, an axis of the second reverse wheel being parallel to the axis of the drive wheel;

a drive member fixedly connected to the bracket, and an output shaft of the drive member being coaxial with and fixedly connected to the drive wheel;

a guide rod fixedly connected to the bracket, wherein an axis of the guide rod is perpendicular to the axis of the drive wheel, and the first reverse wheel and the second reverse wheel are respectively provided near opposite ends of the guide rod;

a slider axially slidable along the guide rod;

a transducer fixedly connected to the slider;

a first rope having two ends of the first rope respectively connected to the drive wheel and the slider, and the first rope being wound on the first reverse wheel;

a second rope, wherein two ends of the second rope are respectively connected to the drive wheel and the slider, and the second rope is wound on the second reverse wheel; the first rope and the second rope are wound on the drive wheel in opposite directions, and the winding direction of the first rope on the first reverse wheel is opposite to the winding direction of the second rope on the second reverse wheel; and at least one elastic member connected to the drive wheel or the slider, at least one end of at least one rope being in buffer connection to the drive wheel or the slider via the elastic member.

2. The linear scanning mechanical volume probe according to claim 1, wherein the drive wheel has a receiving groove, and an opening communicating with the receiving groove is provided on an outer side wall of the drive wheel; one end of the first rope connected to the drive wheel and one end of the second rope connected to the drive wheel respectively have a first chuck, and the first chuck extends into the receiving groove through the opening and abuts against an inner peripheral wall of the receiving groove.

3. The linear scanning mechanical volume probe according to claim 1, wherein the drive wheel has a receiving groove and an opening communicating with the receiving groove is provided on an outer side wall of the drive wheel, one end of the first rope connected to the drive wheel and one end of the second rope connected to the drive wheel respectively have a first chuck, and the first chuck extends into the receiving groove through the opening; a first pin and the elastic member are provided in the receiving groove, the first pin is fixedly connected to the drive wheel, one end of the elastic member is connected to the first pin, wherein the first chuck forms a first clip, and the at least one first clip is connected to the other end of the elastic member.

4. The linear scanning mechanical volume probe according to claim 1, wherein one end of the first rope connected to the slider and one end of the second rope connected to the slider respectively have a chuck, the slider is provided with a slot, and wherein chuck extends into the slot through the slider and abuts against an inner peripheral wall of the slot.

5. The linear scanning mechanical volume probe according to claim 1, wherein one end of the first rope connected to the slider and one end of the second rope connected to the slider respectively have a chuck, wherein the chuck is provided with a clip, a pin is fixed on the slider, and wherein the clip is connected to the pin.

6. The linear scanning mechanical volume probe according to claim 1, wherein one end of the first rope connected to the slider and one end of the second rope connected to the the slider respectively have a chuck, wherein the chuck is provided with a clip, a pin is fixed on the slider, one end of the elastic member is connected to the pin, and one end of the clip is connected to other end of the elastic member.

7. The linear scanning mechanical volume probe according to claim 1, further comprising another guide rod, wherein the two guide rods are provided on the bracket at intervals along an axial direction of the drive wheel, the two guide rods are parallel to each other, and the slider respectively cooperates with the two guide rods.

8. The linear scanning mechanical volume probe according to claim 7, wherein the slider is provided with a through hole through which one of the guide rod passes and a groove cooperating with the other guide rod.

* * * * *